(12) United States Patent  (10) Patent No.: US 8,314,244 B2
Bigot  (45) Date of Patent: Nov. 20, 2012

(54) METHOD FOR PREPARING ACTIVATED ESTERS

(75) Inventor: Antony Bigot, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/140,254

(22) PCT Filed: Dec. 15, 2009

(86) PCT No.: PCT/FR2009/052528
§ 371 (c)(1),
(2), (4) Date: Sep. 6, 2011

(87) PCT Pub. No.: WO2010/076474
PCT Pub. Date: Jul. 8, 2010

(65) Prior Publication Data
US 2011/0313168 A1 Dec. 22, 2011

(30) Foreign Application Priority Data
Dec. 17, 2008 (FR) .................... 08 07090

(51) Int. Cl.
C07D 211/72 (2006.01)
(52) U.S. Cl. ..................... 546/290
(58) Field of Classification Search ........ None
See application file for complete search history.

(56) References Cited
FOREIGN PATENT DOCUMENTS
WO WO2004/016801 A2 2/2004

OTHER PUBLICATIONS

Ogura, Haruo et al., "A Novel Active Ester Synthesis Reagent (N,N'-Disuccinimidyl Carbonate)," Tetrahedron Letters (1979), vol. 49, pp. 4745-4746.
Carlsson, Jan et al., "Protein Thiolation and Reversible Protein-Protein Conjugation N-Succinimidyl 3-(2-Pyridyldithio)Propionate, A New Heterobifunctional Reagent," Biochemical Journal (1978), vol. 173, No. 3, pp. 723-737.
Tokutake, Nobuya et al., "Detection of unusual lipid mixing in cholesterol-rich phospholipid bilayers: The long and the short of it," Journal of the American Chemical Society (2003), vol. 125, No. 30, pp. 8994-8995.
International Preliminary Report on Patentability dated Jul. 5, 2011 issued in PCT/FR2009/052528.

Primary Examiner — Janet Andres
Assistant Examiner — Heidi Reese
(74) Attorney, Agent, or Firm — Scully, Scott, Murphy & Presser P.C.

(57) ABSTRACT

The invention relates to a method for preparing an activated ester of the formula (I), where R is a ($C_1$-$C_6$) alkyl, aryl, heteroaryl, cycloalkyl, or heterocycloalkyl group, and ALK is a ($C_1$-$C_6$) alkylene group, said method consisting of reacting the dicyclohexylamine $P_1$ salt and the disuccinimidyl carbonate (DSC) in a solvent in which the dicyclohexylamine salt of the N-hydroxysuccinimide $P_2$ is precipitated. The invention also relates to products of the formula $P_1$.

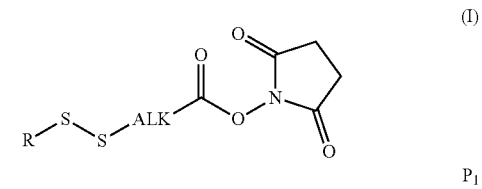

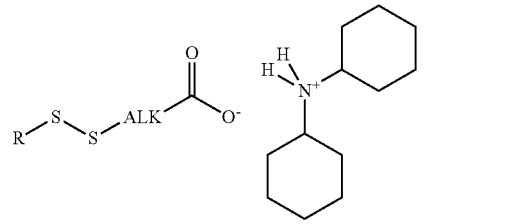

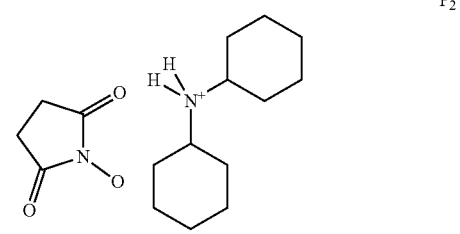

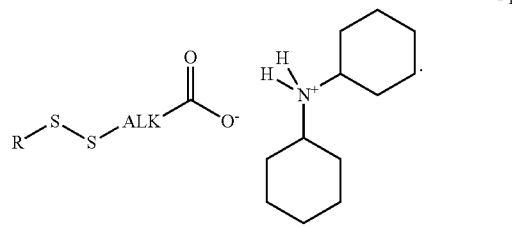

11 Claims, No Drawings

METHOD FOR PREPARING ACTIVATED ESTERS

The present invention relates to the preparation of activated esters of formula (I):

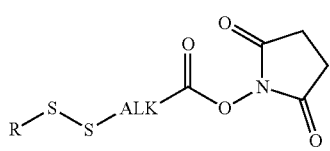
(I)

in which R is a $(C_1-C_6)$alkyl, aryl, heteroaryl, cycloalkyl or heterocycloalkyl group, and Alk is a $(C_1-C_6)$alkylene group. These activated esters can be used in the preparation of conjugates, i.e. of antibodies to which biologically active chemical compounds, such as cytotoxic compounds, are attached by covalent bonding. Further details on conjugate chemistry will be found, for example, in Birch and Lennox, Monoclonal Antibodies: Principles and Applications, Chap. 4, Wiley-Liss, New York, N.Y. (1995).

PRIOR ART

WO 2004/016801 describes activated esters comprising a nitrosuccinimide unit. The preparations of these compounds described in FIGS. 1 to 6 are based on reactions different than those envisioned in the present invention.

*J. Med. Chem.* 2006, 49(14), 4392-4408 describes the preparation of activated esters, in particular N-succinimidyl-[4-methyl-4-(methyldithio)]pentanoate on scheme 6, by means of reactions different than that envisioned in the present invention.

*Langmuir* 2000, 16(1), 81-86 describes, on scheme 1, the preparation of succinimidyl-3-(2-pyridyldithio)butyrate (SPDB) by coupling of the corresponding acid with N-hydroxysuccinimide.

U.S. Pat. Nos. 6,407,263, 5,872,261, 5,892,057 and 5,942,628 describe activated esters and the method for preparing same.

*Can, J. Chem.* 1982, 60, 976 describes the preparation of the dicyclohexylamine salt of N-hydroxysuccinimide ($P_2$) by reaction between dicyclohexylamine and N-hydroxysuccinimide in acetone. This compound has the CAS No. 82911-72-6.

*Can. J. Chem.* 1986, 64(11), 2097-2102; *J. Chem. Soc., Perkin Trans.* 1 1985, 4, 765-8; *Bull. Soc. Chem. Jpn* 1986, 59(8), 2505-8; *Coll. Czech. Chem. Comm.* 1985, 50(12), 2925-2936 describe the preparation of succinimide esters from dicyclohexylamine salts but without using disuccinimidyl carbonate.

*Tetrahedron Letters* 1979, 49, 4745-4746 describes DSC and its value in synthesis (see scheme 2).

*Biochem. J.* 1978, 173, 723-737 describes the preparation of activated esters in the presence of N-hydroxysuccinimide and of dicyclohexylcarbodiimide.

*JACS* 2003, 125(30), 8994-8995 is part of the technical background.

BRIEF DESCRIPTION OF THE INVENTION

The invention relates to a method for preparing an activated ester of formula (I):

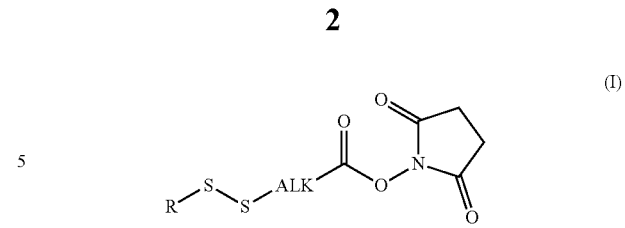
(I)

in which R is a linear or branched $(C_1-C_6)$ alkyl, aryl, heteroaryl, cycloalkyl or heterocycloalkyl group, and Alk is a linear or branched $(C_1-C_6)$alkylene group, said method consisting in reacting the dicyclohexylamine salt $P_1$:

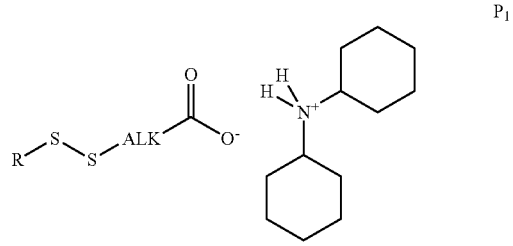
$P_1$ and disuccinimidyl carbonate (DSC) in a solvent in which the dicyclohexylamine salt of N-hydroxysuccinimide $P_2$

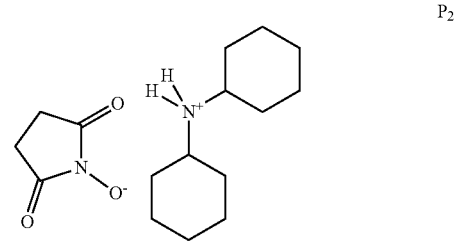
$P_2$ precipitates.

The invention also relates to the products of formula $P_1$:

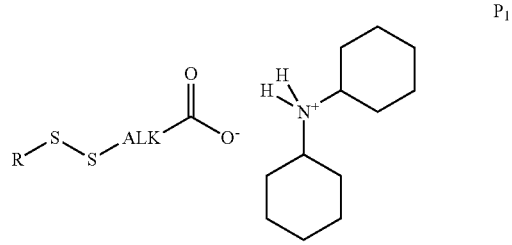
$P_1$ more particularly those of formula:

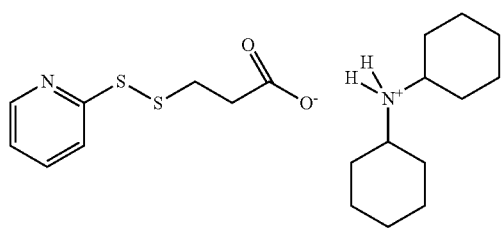

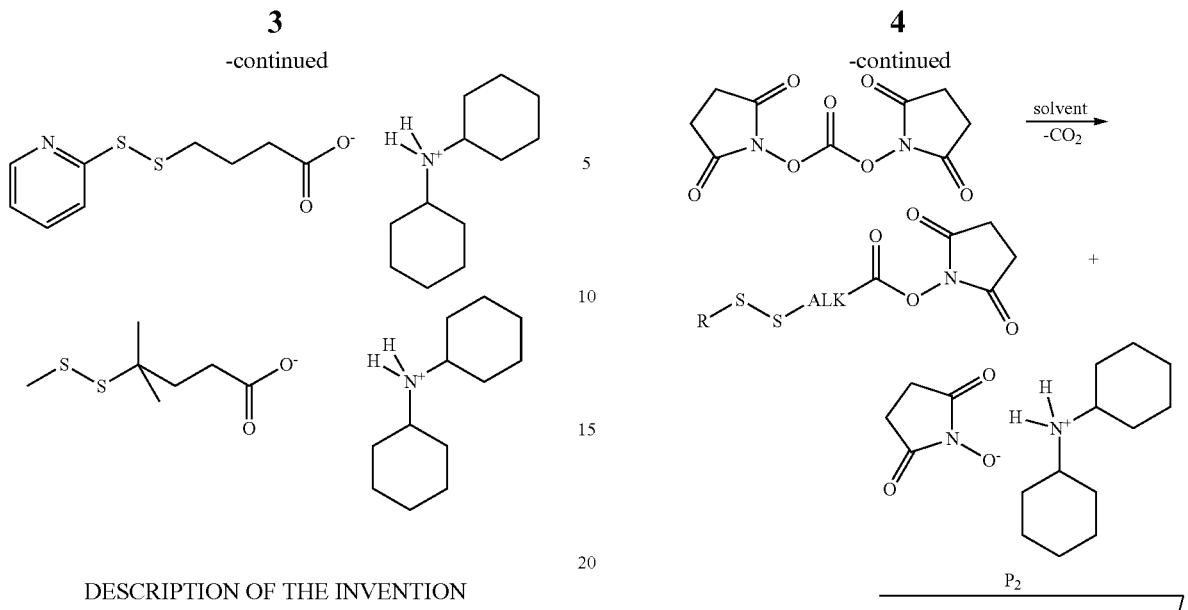

DESCRIPTION OF THE INVENTION

Definitions
- alkyl group: a linear or branched, saturated aliphatic hydrocarbon-based group obtained by removing a hydrogen atom from an alkane. Mention may in particular be made of the following groups: methyl, ethyl, propyl, butyl, pentyl, hexyl, 2-methylbutyl, 2-methylpentyl and 1-methylpentyl;
- alkylene group: a divalent group obtained by removing two hydrogen atoms from an alkane. Mention may in particular be made of the following groups: methylene ($-CH_2-$), ethylene ($-CH_2CH_2-$), n-propylene ($-CH_2CH_2CH_2-$) and butylene ($-CH_2CH_2CH_2CH_2-$);
- cycloalkyl group: a cyclic alkyl group containing from 3 to 10 carbon atoms involved in the cyclic structure. Mention may in particular be made of the following groups: cyclopropyl, cyclopentyl and cyclohexyl;
- aryl group: an aromatic group containing from 6 to 10 carbon atoms. Mention may in particular be made of the following groups: phenyl, naphthyl, indenyl and fluorenyl;
- heteroaryl group: an aromatic group of 5 to 10 ring members comprising, as atoms forming the ring, one or more heteroatoms selected from O, S or N;
- heterocycloalkyl group: a cycloalkyl group as defined above, also comprising, as atom(s) forming the ring, one or more heteroatoms selected from N, O or S.

The preparation is based on the reaction between the dicyclohexylamine salt $P_1$ and disuccinimidyl carbonate (DSC) in a solvent in which the dicyclohexylamine salt of N-hydroxysuccinimide $P_2$ precipitates (scheme 1), Scheme 1

R is:
- a ($C_1$-$C_6$)alkyl group: for example a methyl, ethyl, propyl, butyl or pentyl group, which is optionally branched;
- a ($C_3$-$C_7$)cycloalkyl group: for example the cyclopropyl group;
- an aryl group: for example the phenyl group;
- a heteroaryl group: for example the 2-pyridinyl group
- a heterocycloalkyl group: for example the piperidinyl group.

Alk is a ($C_1$-$C_6$)alkylene group, for example a propylene, butylene or pentylene group, which is optionally branched. It is more particularly the $(CH_2)_n$ group, n denoting an integer ranging from 1 to 6.

The function of the dicyclohexylamine is to promote the reaction and to render insoluble the N-hydroxysuccinimide which is released. This reaction has the following advantages:
- ease of implementation: simple bringing into contact, no heating, slow and controlled release of $CO_2$;
- since the compound $P_1$ is in carboxylate form, it is not necessary to add an additional base in order to activate the reaction;
- the compound $P_2$ which is released has only very low solubility in the solvent used and it precipitates. The majority of $P_2$ can therefore be readily removed by simple mechanical separation, for example filtration;
- the reaction makes it possible to readily obtain the activated ester with a good yield and good purity.

$P_2$ is prepared by neutralization of the corresponding acid with dicyclohexylamine. DSC is a commercial product.

The solvent is advantageously a ketone, which exhibits fewer toxicological problems than the solvents normally used for this type of reaction (dichloromethane or dimethylformamide). The ketone may, for example, be acetone or methyl isobutyl ketone (MIBK). MIBK is preferred because, since it is water-miscible (1.55% w/w at 20° C.), it allows aqueous washing of the product, thus facilitating the removal of residual P$_2$. It also makes it possible to remove the residual water by azeotropic distillation. Finally, MIBK is a good solvent for the activated ester but not for the compounds P$_2$ and P$_1$ and the DSC, which allows a slow and controlled reaction between P$_1$ and the DSC: the reactants can thus be initially mixed in their entirety without this posing a problem in terms of safety (rapid reaction with uncontrolled release of CO$_2$).

The reaction is carried out at ambient temperature (approximately 20° C.). P$_2$ can precipitate spontaneously in certain solvents. In order to promote the precipitation of P$_2$, it is possible, after having reacted P$_1$ and the DSC, to cool the reaction mixture (for example to a temperature close to 0° C.)

This reaction makes it possible in particular to prepare the following activated esters: N-succinimidyl-3-(2-pyridyldithio)propionate (SPDP), N-succinimidyl-3-(2-pyridyldithio)butyrate (SPDB) or N-succinimidyl-[4-methyl-4-(methyldithio)]pentanoate from the corresponding acid salts, namely, respectively:

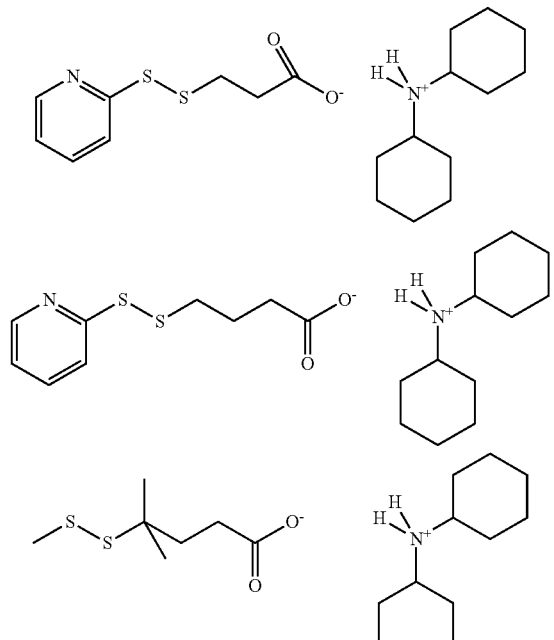

EXAMPLES

Example 1: Preparation of N-succinimidyl-[4-methyl-4-(methyldithio)]pentanoate

The reaction is the following:

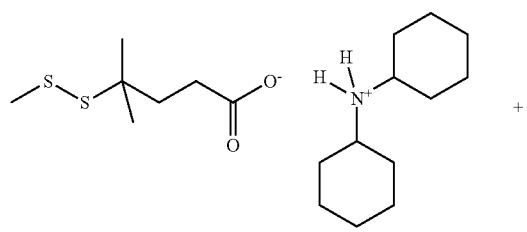

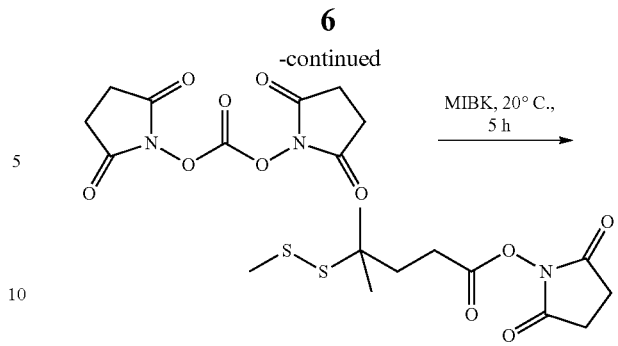

A suspension of the dicyclohexylamine salt of 4-methyl-4-(methyldithio)pentanoic acid (23 g) and DSC (18.2 g, 1.1 eq.) in 161 ml of MIBK is stirred at approximately 20° C. for 5 h. The suspension is then cooled to approximately 0° C., stirred for 1 h at this temperature, and then filtered.

The solid is washed with 2×23 ml of MIBK. The organic phases are combined, and washed with 2×58 ml of a 6N aqueous solution of HCl and then with 92 ml of demineralized water. The organic phase is then concentrated to dryness under vacuum. The resulting solid is solubilized in 230 ml of dichloromethane (DCM), and the resulting solution is treated with 46 g of silica and stirred for 10 min, and then the silica is filtered off and washed with 2×69 ml of DCM. This operation is repeated a second time. The organic phase is then concentrated to approximately half the volume, and then, at approximately 20° C., 391 ml of n-heptane are added in approximately 30 min. The resulting white suspension is stirred at this temperature for approximately 1 h, cooled to approximately −10° C. over the course of approximately 1 h, and then stirred at this temperature for approximately 1 h. The solid is then filtered off, washed with 2×23 ml of n-heptane cooled to approximately −10° C., and then dried under vacuum at 40° C. for 15 h. The 4-N-hydroxysuccinimidyl-[4-methyl-4-(methyldithio)]pentanoate is isolated with a yield of 70.6%. Its purity, determined by HPLC, is 99.65% (excluding solvents).

Example 2: Preparation of N-succinimidyl-3-(2-pyridyldithio)butyrate (SPDB)

The reaction is the following:

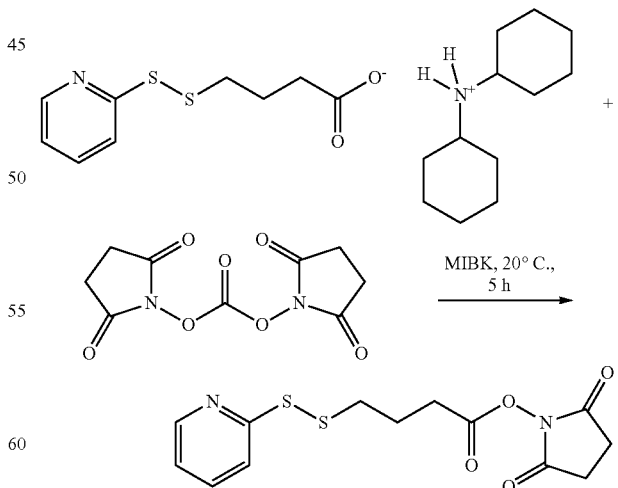

The dicyclohexylamine salt (40 g, 1 eq.) and the DSC (28.7 g, 1.1 eq.) are suspended in 280 ml of MIBK. The mixture is stirred for 4 h at 20±3° C. The suspension is cooled to 0±3° C., left at this temperature for 30 min and filtered, and the solid obtained is washed with ice-cold MIBK (120 ml). The mother liquors are washed with water (3×176 ml) and evaporated to dryness under reduced pressure on a rotary evaporator with a bath at 50° C. until an amount of MIBK of ≦2.5% is obtained. The crude SPDB is obtained in the form of a yellow oil.

The SPDB (32.5 g) is then dissolved in ethanol (455 ml) at 35±2° C. The solution obtained is cooled to 18±2° C.: the pure SPDB begins to crystallize. 90 ml of n-heptane are added over the course of 10 min, the crystallization intensifies. The mixture is cooled to 0±3° C. and 820 ml of n-heptane are added over the course of 20 min. The mixture is stirred for 1 h at 0±3° C. The pure SPDB is isolated by filtration, washed with 2×90 ml of ice-cold n-heptane and dried in an oven (30° C., 50 mbar). Yield: 84.8%, HPLC purity: 98.7%.

The invention claimed is:

1. A method for preparing an activated ester of formula (I)

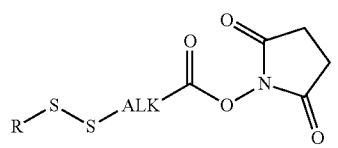
(I)

in which R is a linear or branched ($C_1$-$C_6$)alkyl, aryl, heteroaryl, cycloalkyl or heterocycloalkyl group, and Alk is a linear or branched ($C_1$-$C_6$)alkylene group,
comprising reacting the dicyclohexylamine salt $P_1$:

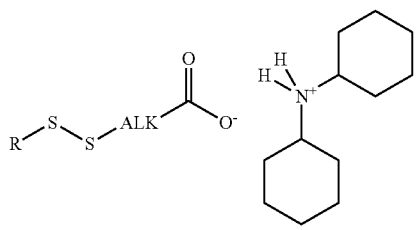
$P_1$ and disuccinimidyl carbonate (DSC) in a solvent in which the dicyclohexylamine salt of N-hydroxysuccinimide $P_2$

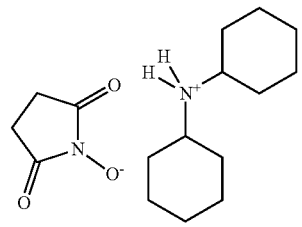
$P_2$ precipitates.

2. The method as claimed in claim 1, wherein R is a methyl, ethyl, propyl, butyl or pentyl group, which is optionally branched, or the 2-pyridinyl group.

3. The method as claimed in claim 1, wherein Alk is a propylene, butylene or pentylene group, which is optionally branched.

4. The method as claimed in claim 1, wherein Alk is the $(CH_2)_n$ group, n denoting an integer ranging from 1 to 6.

5. The method as claimed in claim 1, wherein the reaction is carried out in a ketone.

6. The method as claimed in claim 5, wherein the ketone is MIBK.

7. The method as claimed in claim 1, wherein after having reacted $P_1$ and DSC, the reaction mixture is cooled in order to promote the precipitation of $P_2$.

8. The method as claimed in claim 1, wherein $P_2$ is removed by mechanical separation.

9. The method as claimed in claim 8, wherein the mechanical separation is filtration.

10. A product of formula $P_1$:

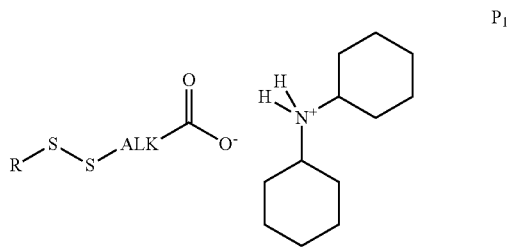
$P_1$ wherein R is a linear or branched ($C_1$-$C_6$) alkyl, aryl, heteroaryl, cyloalkyl or heterocycloalkyl group, and Alk is a linear or branched ($C_1$-$C_6$) alkylene group.

11. The product as claimed in claim 10, of formula:

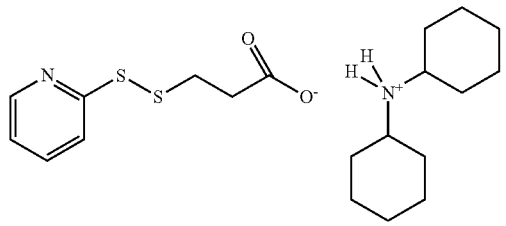

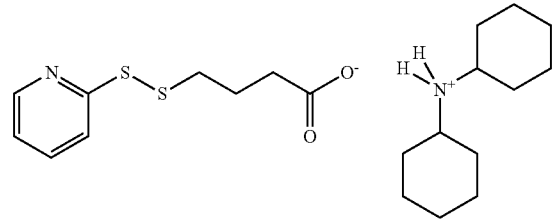

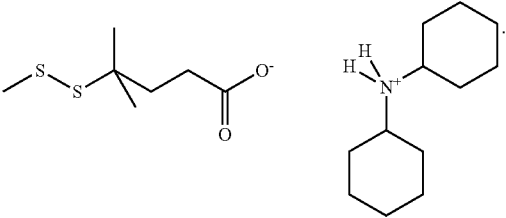

* * * * *